United States Patent [19]
Brown et al.

[11] Patent Number: 5,455,513
[45] Date of Patent: Oct. 3, 1995

[54] SYSTEM FOR MEASURING PROPERTIES OF MATERIALS

[75] Inventors: Neil L. Brown, Falmouth; Alan J. Fougere, N. Falmouth, both of Mass.

[73] Assignee: Falmouth Scientific, Inc., Falmouth, Mass.

[21] Appl. No.: 163,356

[22] Filed: Dec. 7, 1993

[51] Int. Cl.$^6$ ............................ G01N 27/02; G01R 27/22
[52] U.S. Cl. ........................ 324/445; 324/99 D; 324/693
[58] Field of Search ..................................... 324/445, 339, 324/99 R, 99 D, 663, 691, 693

[56] References Cited

U.S. PATENT DOCUMENTS 4,370,892  2/1983  Schmoock ............................. 324/99 D

*Primary Examiner*—Ernest F. Karlsen
*Attorney, Agent, or Firm*—Henry D. Pahl, Jr.

[57] ABSTRACT

A system for determining a property, such as conductivity, of a material in which a sensor provides a square wave sensor output signal the value if which is selected to the proper in response to a square wave driver signal. The sensor output signal is compared with a feedback signal to produce an error signal. A forward circuit responds to the error signal and provides an in-phase component thereof which is integrated to provide an integrated DC output signal. A feedback signal provides an in-phase square wave feedback signal the peak-to-peak amplitude of which has a precisely selected relationship with the integrated DC output signal for comparison with the square wave sensor output signal to reduce the error signal to zero. The integrated DC output signal can be digitized and suitably processed to provide a signal which represents the property of the material to a high degree of accuracy.

11 Claims, 4 Drawing Sheets

SYSTEM FOR MEASURING PROPERTIES OF MATERIALS

INTRODUCTION

This invention relates generally to techniques for measuring properties of materials, and more particularly, to a technique for making electrical conductivity measurements in fluids using contacting or non-contacting sensors.

BACKGROUND OF THE INVENTION

Industrial process control systems have often required the measurement of the electrical conductivity of materials, such as fluids, used in the system. In the past, these measurements have been made by using sensors which fall into one of two categories, i.e., contacting sensors and non-contacting sensors. Contacting sensors rely on the electrical contact of the measurement electronics to the material, e.g., a conductive fluid, via one or more sets of electrodes positioned in the material at fixed distances from each other. A voltage is applied across one set of electrodes and the induced current in the material is measured either across the electrodes or alternatively through a second set of electrodes, the measured flow of electrical current being proportional to the conductivity. Non-contacting sensors utilize two inductors, or transformers, one of which is used to induce voltage in the material and the second one of which is used to measure the resultant flow of current which occurs in the material.

In the past, implementations of such systems often are not satisfactory, particularly when using non-contacting sensors, because of the inherent lower sensitivity of inductive sensors, especially when measuring very low conductivities. Moreover, prior art non-conducting sensors normally have large physical geometries which are needed to overcome the sensitivity limitations of smaller sensor configurations.

In addition, in prior systems, measurement errors arise which are due to errors generated by the electronic circuitry that is used in such systems. Prior systems normally do not effectively address such problems when using either type of sensors and, hence, the accuracy of the measurements made by such systems is unacceptable in many applications. In the prior art, the electronics are typically configured as shown in FIG. 1 as a "feed forward" circuit where a signal generator 10 is used to drive a voltage Vi across a drive coil 11, which results in a current Is flowing in a material, e.g., a conductive solution 12, represented as flowing in a loop having a solution conductivity I/Rs, which current is proportional to the conductivity Gs of the solution. The presence of the current Is results in a current Im flowing in the sensor coil 13 which is measured by a suitable current meter 14 and found to be proportional to the conductivity of the solution. In this circuit there are many sources of errors, many of which are related to the magnetic properties of the transformers, which errors have limited their accuracy in the past.

It is desirable to devise a system which can utilize sensors in a manner so as to provide a highly accurate measurement of electrical conductivity even at relatively low conductivity levels, and even when using relatively small non-contacting sensors.

BRIEF SUMMARY OF THE INVENTION

In accordance with the invention, a system utilizes a sensor with a material whose conductivity is to be measured, which sensor is driven by a drive signal which has a square wave signal waveform. An error signal produced at the output of the sensor (as discussed below) is used to derive a DC system output signal which is proportional to the electrical conductivity of the material, which output signal can be suitably digitized and processed, e.g., by an appropriate microprocessor, to provide the desired conductivity value.

The system output is used to derive an in-phase square wave feedback signal which is supplied via a suitable feedback path to the output of the sensor to produce an error signal at the sensor output which is the difference in the current in the sensed output and the current in the feedback path. The peak-to-peak amplitude of the feedback square wave signal is made equal to the amplitude of the DC system output signal. The use of a square wave drive signal and a square wave feedback signal, where the ratio of the peak-to-peak amplitude of the square wave to the amplitude of the DC signal is precisely selected, assures greater accuracy in the system output signal. A calibration circuit can be used to accurately simulate the output of the sensor at several different but exactly known material conductivities.

DESCRIPTION OF THE INVENTION

The invention can be described in more detail with the help of the accompanying drawings wherein.

Figure 2:
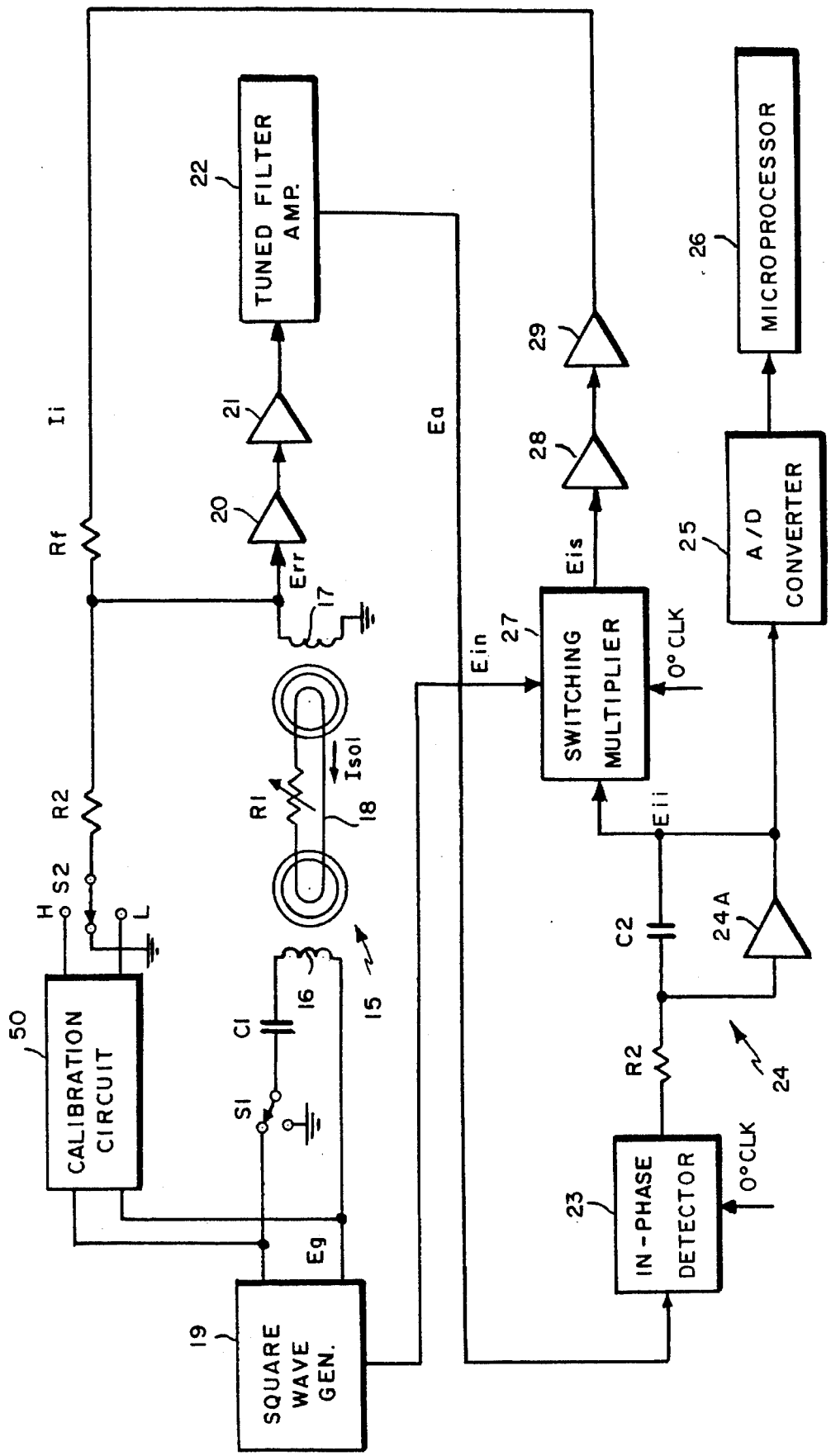
FIG. 2 shows sensing circuitry depicting one embodiment of the invention.

As can be seen in FIG. 2, which represents one embodiment of the invention, a current conductivity sensor 15 is an inductively coupled sensor consisting of co-axial toroidal windings, or transformers 16 and 17 with a conductive fluid in effect forming a single turn circuit 18 having a conductivity Gs linking both transformers. A square wave signal having a selected frequency, e.g., 2048 Hz, is applied from a signal generator 19 to the input winding 16 of the sensor which in turn produces a signal in the conductive fluid whose electrical conductivity is to be measured. The signal in the fluid is equal to the signal generator output voltage Eg divided by the number of turns on the input winding of the sensor. This operation results in producing a current Isol in the fluid, e.g., a conductive solution, given by the following equation:

$$Isol = Eg * G * Kc / Np$$

where Eg is the square wave generator voltage, G is the conductivity of the solution, Kc is the cell constant of the conductivity sensor and Np is the number of turns on the input winding of the sensor.

The signal induced in the output winding 17 of the sensor is amplified by a pre-amplifier 20 the output thereof being further amplified by a fixed gain amplifier 21. The output of amplifier 21 is supplied to a tuned filter amplifier 22 which is tuned to the same frequency as that of the signal from square wave generator 19 to effectively remove harmonic and sub-harmonic frequency components so as to produce a substantially sine wave voltage signal Ea which has primarily an in-phase component and a relatively small quadrature component.

The signal Ea is supplied to an appropriate in-phase detector 23 to produce a DC signal proportional to the in-phase component of Ea which is then integrated by an integrator circuit 24, comprising resistance R2, capacitance C2 and op-amp 24A, to produce an integrated analog DC output signal Eii. Eii is applied to the input of a switching multiplier, the peak-to-peak amplitude of the square wave output of which is exactly equal to the amplitude of the DC output of the integrator. Eis is 180 degrees out of phase with the error signal Err and, hence, through negative feedback action exactly balances the circuit, leaving Err exactly at zero.

In order to achieve an accurate measurement of the electrical conductivity, the integrated output Eii is fed back to provide a current at feedback resistor Rf which current is effectively subtracted from the current of the sensor output signal to produce an error signal in the form of a voltage Err at the input to pre-amplifier 20 so as to maintain the error signal essentially at a zero value, or a value as small as possible. In order to do so, the output signal Eii is supplied to a switching multiplier 27 driven by an in-phase reference signal Ein from square wave generator 19 so as to produce an in-phase voltage signal Eis, the peak-to-peak amplitude of which is exactly equal to the amplitude of the integrated DC output signal Eii.

The square wave voltage signal Eis is supplied to a preamplifier 28 and to an attenuation amplifier 29 having a fixed attenuation substantially equal to the reciprocal of the fixed gain of the feed forward amplifier 21. The output of attenuation amplifier 29 is supplied via feedback resistor Rf to the output winding 17 of sensor 15 so that, as mentioned above, the feedback current is effectively subtracted from the current in the output winding 17 to produce the error signal Err. While any effective switching multiplier which is known to the art can be used in the feedback circuit, one suitable known switching amplifier is fully described in U.S. Pat. No. 3,940,693 issued on Feb. 24, 1976 to N. L. Brown. By using a square wave drive at sensor 15, a square wave feedback voltage from switch multiplier 26 that has a peak-to-peak amplitude exactly equal to the integrated DC amplitude of the output signal representing the electrical conductivity, and a feedback circuit having a substantially constant overall loop gain (i.e, forward gain plus feedback gain), it is found that the circuitry depicted in FIG. 2 provides a more accurate measurement of the conductivity of the material in question than provided in prior art devices. Such circuitry can be useful in many applications. In such a case the fixed forward gain and the feedback attenuation are set to values which provide effective conductivity measurements over a particular range of conductivities, the gain and attenuation values being changed when used over other conductivity ranges.

The circuitry of FIG. 2 includes, as an optional portion thereof, a calibration circuit 50, the operation of which is discussed in more detail below. If such calibration circuit is used in the system, the overall circuitry is placed in a measurement mode of operation when the switches S1 and S2 are in the positions depicted in the drawing, while the overall circuitry is placed in a calibration mode of operation when such switches are in their alternative positions. Operation in the calibration mode is discussed below.

Figure 1:
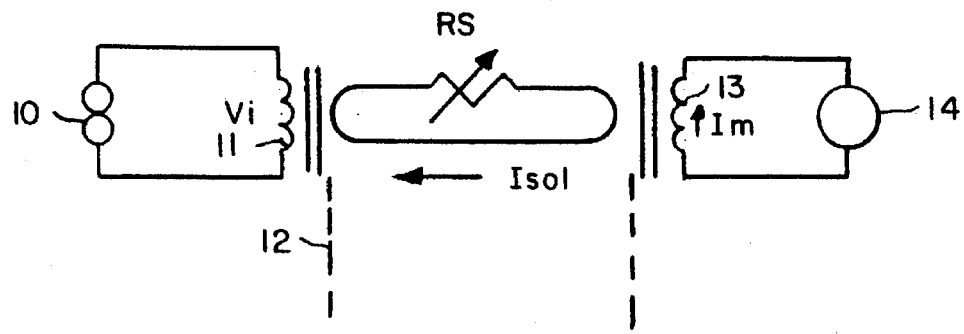
FIG. 1 shows sensing circuitry of the prior art.
Figure 3:
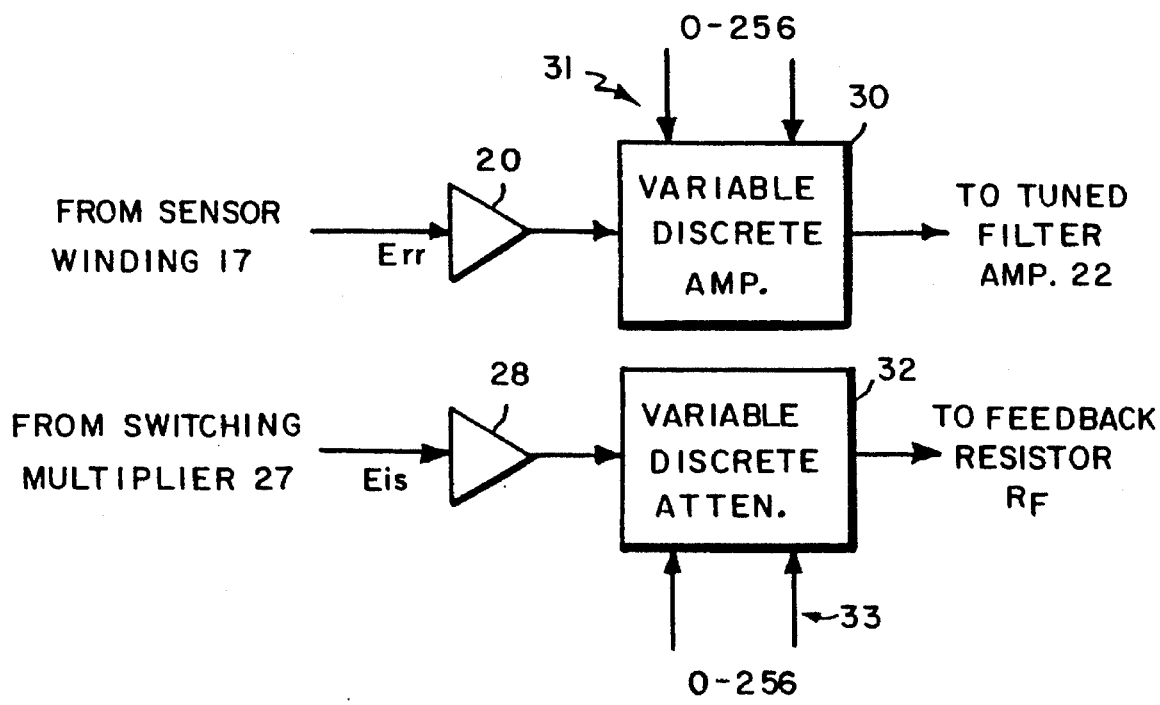
FIG. 3 shows alternative portions of sensing circuitry of FIG. 1 to provide a further embodiment of the invention.

In order to provide a measurement system for producing desired output voltage signals over a wider range of conductivities, the circuitry of FIG. 2 can be modified as shown in FIG. 3 which depicts only certain portions of the circuitry of FIG. 2. As seen therein, fixed gain amplifier 21 of FIG. 2 can be replaced by a discretely variable amplifier, i.e., an amplifier having a gain which can be discretely varied over a plurality of ranges using a digital control signal therefor. For example, a discretely variable amplifier 30 is connected to preamplifier 20 and has a digital signal 31 supplied thereto to control the gain thereof over a selected range of digital levels, e.g., the digital signal may have digital values from 0 to 256 to control the gain over such number of range levels.

In a similar manner, the fixed attenuation amplifier 29 is replaced by a discretely variable attenuation amplifier 32, the attenuation of which is varied discretely over a plurality of ranges using a digital control signal therefor. Variable attenuation amplifier 32 is connected to preamplifier 28 and has a digital control signal 33 supplied thereto to control the attenuation thereof over a selected ranges of levels, e.g., a digital control signal having digital values from 0 to 256 to control the attenuation over such range of digital values.

The digital control signal appropriate for any particular range portion of the overall range of conductivities that can be measured by the system can be supplied by using microprocessor 26. As an example of such use in the exemplary implementation of FIG. 3, for use with an exemplary geometry inductive conductivity sensor having a low range of 0–25 microSiemens/meter (µS/m) and a high range of 0–3000 mS/m, the total range is separated into $2^8$ successive ranges, each successive range overlapping the preceding range. In each range the value of the forward gain is matched to an appropriate value of feedback attenuation which results in the overall loop gain being maintained at a substantially constant value. For example, a high forward gain coupled with a high feedback attenuation is preferred for very low range conductivities, while a low forward gain coupled with a low feedback attenuation is preferred for very high range conductivities.

At the beginning of a measurement cycle, the microprocessor is programmed to select the gain and attenuation values at the lowest of the $2^8$ ranges. The DC output voltage Eii is examined to see if it is in excess of a full scale level for such range. If it is beyond the full scale range and above acceptable limits for the operation of the A/D converter, the processor continues such measurements for each successive higher range until the value of Eii is acceptable, i.e., it lies below the full scale value and within the acceptable limits of the A/D converter. The appropriate digital control inputs for amplifier 30 and alternator 32 are then used for operation. If the output value Eii exceeds the full scale limit or drops below the lowest scale limit for that range, the microprocessor again selects the appropriate range of operation by using the same kind of successive approximation technique. Programming of the microprocessor to provide such known successive approximation operation would be well within the skill of those in the art.

Figure 4:
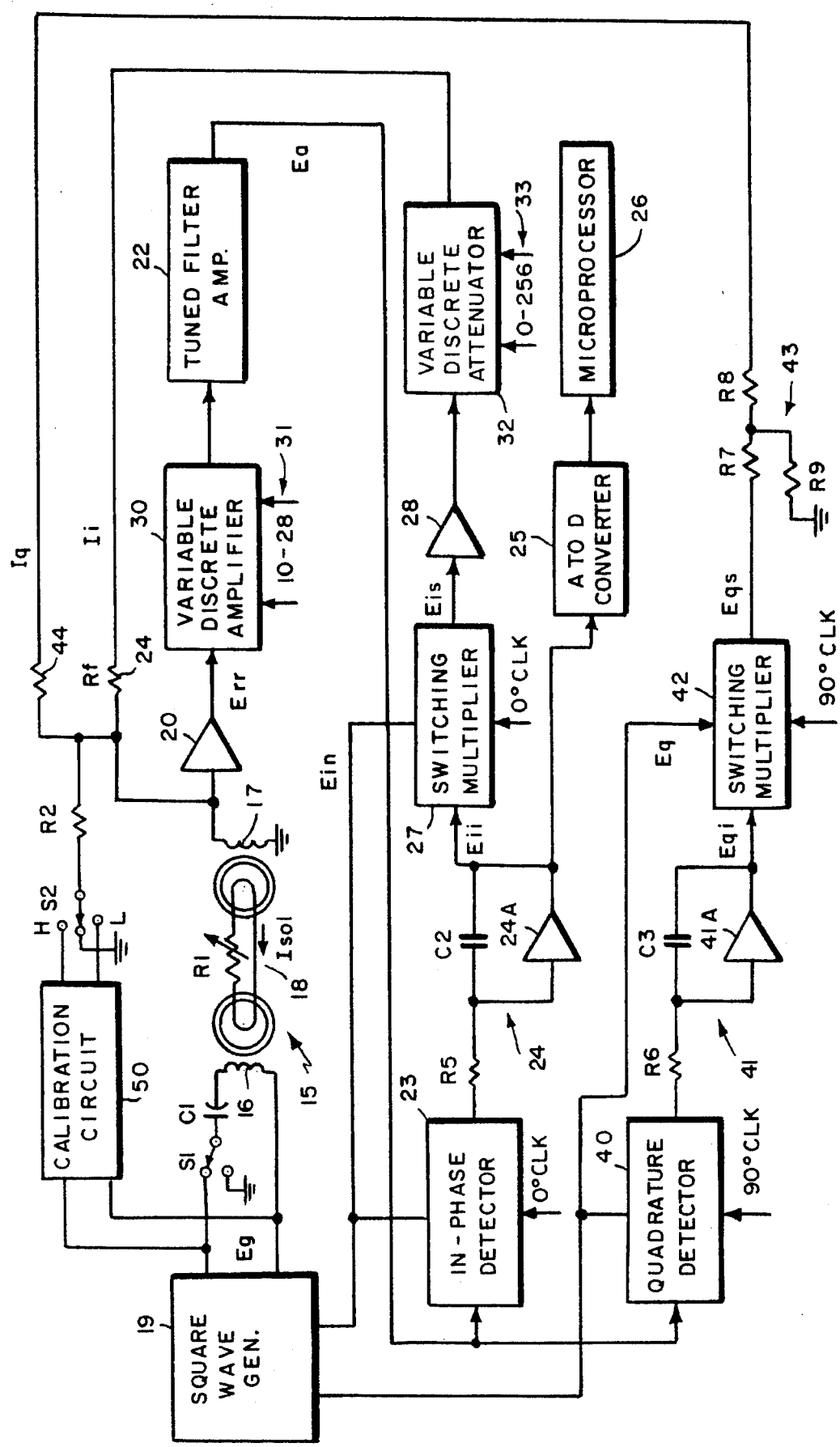
FIG. 4 shows sensing circuitry representing a further embodiment of the invention.

In a still further embodiment of the invention it may be necessary to achieve an even higher accuracy of measurement which takes into account errors which may arise due to stray capacitances in the circuitry. For such purpose, a further feedback circuit is utilized as shown in FIG. 4. As seen therein in the context of the use of the variable gain and variable attenuation amplifiers depicted in FIG. 3, a quadrature feedback circuit is used. In accordance therewith, a quadrature voltage signal is provided in response to the quadrature component of the signal Ea from tuned filter amplifier 22 using a suitable quadrature detector 40, the output of which is integrated in integrator circuitry 41, comprising resistance R6, capacitance C3 and op-amp. 41A, to produce an integrated DC quadrature voltage output signal Eqi. The quadrature signal Eqi is supplied to a switching multiplier 42 of the type disclosed above, which is supplied with a quadrature square wave reference voltage Eq from square wave voltage generator 19, to produce a square wave quadrature feedback signal Eqs having a peak-to-peak amplitude which is equal to the amplitude of integrated D-C quadrature signal Eqi. The feedback signal Eqs produces a quadrature feedback current Iq via resistance network 43 and quadrature feedback resistor 44. The feedback current is supplied to the input of preamplifier 20 to provide a quadrature feedback current which is effectively subtracted from the quadrature current component at the sensor output at winding 17. The use of such quadrature feedback circuitry allows reduction of the quadrature error voltage found at amplifier 20 allowing increased gain to be used in the feed forward section of the circuit to prevent saturation of any of these components due to the amplification of the quadrature error components. Increased amplification allows for high precision to be obtained as a direct result of higher overall loop gains which can be achieved.

As mentioned above, calibration checks can be made using calibration circuit 50 as shown in the drawings. The calibration circuit comprises a number of precision resistors which are selected and configured to simulate the output of the sensor at specific values of conductivity in the fluid. The resistors used should have both low temperature coefficients and low long term drifts so they can accurately re-simulate these values of conductivity at any time after an initial calibration.

Calibration circuit 50 can be placed in use by appropriate settings of switches S1 and S2. When these switches are placed in the positions shown in FIGS. 2 and 4, the calibration circuit 50 is not used and the system operates so as to make the conductivity measurements as desired, as discussed above. To place the calibration circuit into use switch S1 is placed in its grounded position while switch S2 can be placed either in its upper or its lower positions in combination with resistor R2 so that the output thereof in both the upper and lower positions is connected to the input of preamplifier 20. The output Eq of square wave generator 19 is supplied to the input of calibration circuit 50 so as to produce therefrom a square wave signal which exactly simulates the signal which would be produced at a selected known range of conductivity levels of the material. That is, when switch S2 is in its upper H position, a signal is provided at preamplifier 20 for a known maximum (high) conductivity level $C_{kH}$ of the selected range and, when switch S2 is in its lower L position, a signal is provided at preamplifier 20 for the known minimum (low) conductivity level $C_{k2L}$ of the selected range. Thus, specific known output voltage signals $E_{iiH}$ and $E_{iiL}$ at such maximum and minimum conductivities will be produced at the output of integrator circuit 24. The range is selected to be small enough so that the relationship of the known conductivity $C_k$ as a function of the calibration output voltage $E_{ii}$ is a linear function, i.e., $$C_k = M*E_{ii} + B.$$

Calibration measurements of the voltages $E_{iiH}$ and $E_{iiL}$ thus made at the maximum and minimum known conductivities $C_{kh}$ and $C_{kl}$ will permit M and B to be calculated.

Using such values, the values of M and B and the measured output voltages $E_{iiH}$ and $E_{iiL}$ at maximum and minimum levels) can be used to provide the calibrated conductivity at both the maximum and minimum conductivity levels of the range involved;

$$C_H = M*E_{iiH} + B$$

$$C_L = M*E_{iiL} + B.$$

At the time of manufacture the representative value of the resistors in the calibration circuit 50 can be obtained by placing the sensor in a known fluid and measuring both the sensor output and the calibration output. The representative values for the resistor can then be computed by the reverse formula allowing the user to specifically determine values for the calibration circuit resistances in the same units as the required output. In the implementation discussed above only two such points for each range are required when there is a high linearity of operation of both the sensor and circuitry over each of the ranges involved. However, the number of calibration points used can be increased based upon the complexity of a non-linear sensor response to the changes in the properties of the materials measured. The calibration circuit may not be required in applications where the very high absolute accuracy of the circuitry is not needed. Accordingly, the calibration circuit is an optional enhancement to the basic embodiments of the invention.

Figure 5:
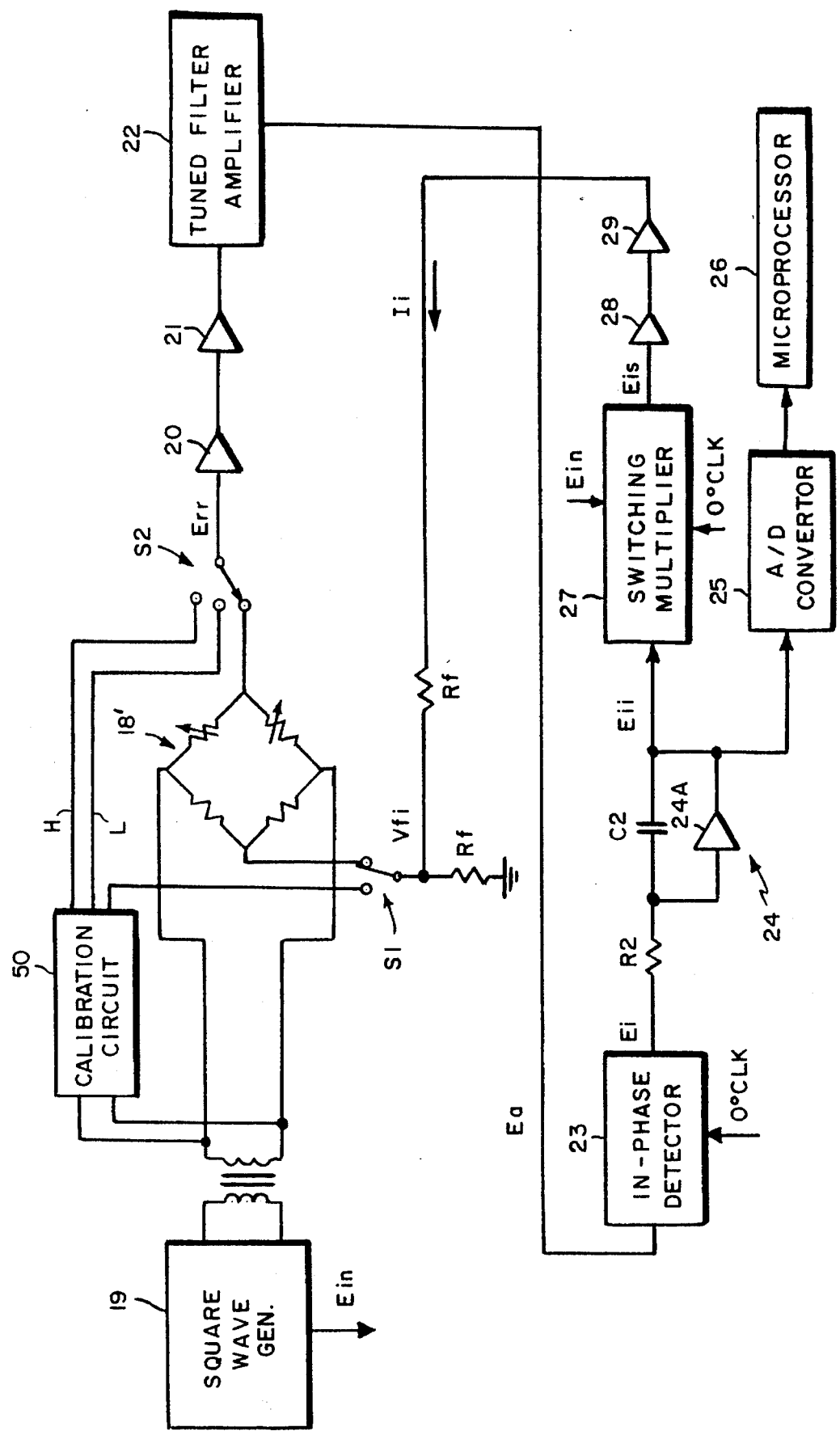
FIG. 5 shows sensing circuitry as used with any four terminal sensors.

FIG. 5 shows still another embodiment of the invention, based for simplicity on the embodiment of FIG. 2. As shown therein the circuitry can be used with any general 4-terminal voltage sensor for providing a voltage output signal, a particular sensor being represented by 4-terminal bridge 18'. While the specific sensor 18 is shown with two active bridge arms, it is understood that, depending on the particular sensor used, there may be 1, 2, 3 or 4 active arms. Using switches S1' and S2' the overall circuitry provide a square wave input to sensor 18' and is arranged to provide a square wave feedback signal so as to reduce the error at preamplifier 20 to achieve an operation similar to that discussed with reference to FIG. 2, as would be understood by those in the art. Appropriate circuitry using the variable gain and variable attenuation of FIG. 3 and quadrature feedback of FIG. 4 can also be used with such a general four-terminal sensor.

While the embodiments of the invention as described above represent preferred embodiments, modifications thereof may occur to those in the art within the spirit and scope of the invention. Thus, while the invention is specifically described as using non-contacting sensors, contacting sensors can also be used. Moreover, while the system is described as being used for measuring electrical conductivities of fluids, e.g., conductive solutions, other physical or chemical properties of various materials, using suitable sensors therefor, can be measured using the system of the invention. Hence, the invention is not to be construed as limited to the specific embodiments described except as defined by the appended claims.

What is claimed is:

1. A system for determining a property of a material comprising:

a sensor positioned in signal contact with said material for providing an output signal, the value of which is related to said property in response to an input driver signal;

a square wave generator for providing a square wave input driver signal having a selected frequency to said sensor to provide a square wave output signal from said sensor;

means responsive to said sensor output signal and to a feedback signal to produce an error signal;

a forward circuit responsive to said error signal for providing a forward signal having an in-phase and a quadrature component each having a substantially sine wave configuration;

an integrator responsive to the in-phase component of said forward signal for integrating said in-phase component to produce an in-phase integrated analog DC output signal;

a feedback circuit responsive to said in-phase integrated analog DC output signal to provide an in-phase square wave feedback signal at said selected frequency, the peak-to-peak amplitude of which has a precisely selected relationship with the amplitude of the DC output signal, for comparison with the in-phase component of the square wave output signal from said sensor to produce said error signal;

an analog-to-digital converter responsive to said in-phase analog DC output signal for providing a digital output signal; and a processor responsive to said digital output signal for processing said digital output signal to provide a processed signal representing the property of said signal.

2. A system in accordance with claim 1 wherein the peak-to-peak amplitude of the square wave feedback signal is selected to be exactly equal to the amplitude of the DC output signal.

3. A system in accordance with claim 1 wherein said forward circuit includes a detector for detecting the in-phase component of said forward signal for supply to said integrator.

4. A system in accordance with claim 3 wherein said forward circuit further includes a filter amplifier responsive to said error signal for removing harmonic and sub-harmonic frequency components from said error signal to provide a filtered forward signal to said detector.

5. A system in accordance with claims 1, 2, 3 or 4 wherein said feedback circuit includes a switching amplifier responsive to an in-phase square wave signal from said square wave generator and to said in-phase analog DC output signal to produce an in-phase square wave signal; and an attenuator having a fixed attenuation and responsive to said in-phase square wave signal for producing an attenuated in-phase square wave feedback signal, the fixed attenuation of said attenuator being selected so that the feedback gain of the feedback circuit is equal to the forward gain of the filter amplifier circuit.

6. A system in accordance with claim 5 wherein the forward gain of the forward circuit and the feedback gain of the feedback circuit are selected to provide measurements of the property of the material over a selected range of values of said property.

7. A system in accordance with claim 6 wherein the property of said circuit is the conductivity thereof and the sensor is a conductivity sensor which provides a square wave output signal the peak-to-peak value of which is related to the conductivity of said material.

8. A system in accordance with claim 7 wherein the forward circuit has a gain which can be discretely varied over a plurality of discrete ranges thereof and the attenuator of the feedback circuit has an attenuation which can be discretely varied over a plurality of discrete ranges thereof, said gain and attenuation being selected for each of said ranges so that the forward gain of the forward circuit and the feedback gain of the feedback circuit provide an overall loop gain having the same substantially constant value for each discrete range.

9. A system in accordance with claim 8 and further including a further integrator responsive to the quadrature component of said forward signal for integrating said quadrature component to produce an integrated quadrature analog DC output signal; and a further feedback circuit responsive to a quadrature square wave signal from said square wave generator and to said quadrature component of said DC output analog signal to provide a quadrature square wave feedback signal at said selected frequency for comparison with a quadrature component of the square wave output signal from said sensor to reduce the quadrature component of said error signal so as to prevent saturation of said forward circuit and to permit the use of a relatively high gain in said forward circuit for providing relatively high precision measurements of said conductivity.

10. A system in accordance with claim 1 wherein said sensor is a current sensor for providing a current output signal.

11. A system in accordance with claim 1 wherein said sensor is a voltage sensor for providing a voltage output signal.

* * * * *